United States Patent [19]

Jordan, Jr.

[11] 4,010,162
[45] Mar. 1, 1977

[54] SUBSTITUTED PHENANTHROLINE PIGMENTS

[75] Inventor: James J. Jordan, Jr., Livingston, N.J.

[73] Assignee: Allied Chemical Corporation, Morris Township, N.J.

[22] Filed: Oct. 20, 1975

[21] Appl. No.: 623,701

Related U.S. Application Data

[63] Continuation-in-part of Ser. No. 508,481, Sept. 23, 1974, abandoned.

[52] U.S. Cl. .............................. 260/272; 260/282; 106/288 Q
[51] Int. Cl.² ....................................... C07D 471/16
[58] Field of Search ........................... 260/282, 272

[56] References Cited

UNITED STATES PATENTS 3,931,186  1/1976  Fuchs et al. ....................... 260/282
3,935,226  1/1976  Jordan, Jr. ......................... 260/282

Primary Examiner—Donald G. Daus
Assistant Examiner—Mark L. Berch
Attorney, Agent, or Firm—Anthony J. Stewart; Jay P. Friedenson

[57] ABSTRACT

Substituted phenanthroline pigments having the formula

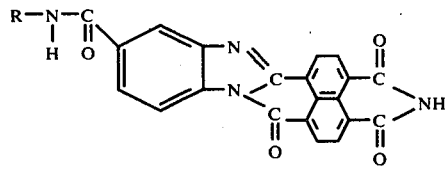

wherein R is a substituted or unsubstituted phenyl or anthraquinonyl, are strong bright yellow to brown in shade and exhibit outstanding fastness to light.

19 Claims, No Drawings

SUBSTITUTED PHENANTHROLINE PIGMENTS

This application is a continuation-in-part of Ser. No. 508,481, filed Sept. 23, 1974, now abandoned.

This invention relates to novel pigment compositions. More particularly this invention relates to pigments comprising novel substituted phenanthroline compounds.

Pigments which are employed in automotive finishes desirably possess certain properties that render them particularly useful for this purpose. Ordinarily, they should be relatively, if not entirely, insoluble in organic solvents, heat-stable, give a strong shade and exhibit fastness to light. While there are numerous pigments in use today for automotive finishes, many of which possess all of these characteristics, much effort is constantly being expended to develop new pigments which qualify for this use. Lightfastness being probably the most important single characteristic in automotive finishes, it is this feature that is the most sought after as new pigment compositions are developed.

BRIEF DESCRIPTION OF THE INVENTION

Briefly, in accordance with this invention there is provided novel compounds, useful as pigments, having the formula:

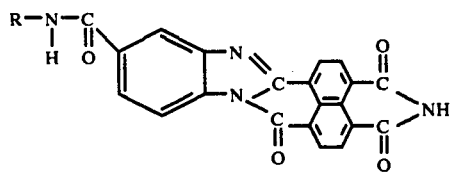

wherein R is phenyl, or anthraquinonyl, unsubstituted or substituted with one to three substituents selected from chloro, nitro, methyl or methoxy. These compounds give a strong bright yellow to brown shade, are insoluble in organic solvents, stable to heat and exhibit excellent lightfastness. Particularly preferred are those compounds wherein R is disubstituted phenylene, i.e., 9-[1'-phenyl (disubstituted) carbamoyl]-benzimidazo[2,1-b]-2-hydrobenzo [[1mn]-3,8-phenanthroline-1,3,6-trione.

DETAILED DESCRIPTION OF THE INVENTION

The compounds of this invention may be prepared by condensing acenaphtene with dimethyl carbamoyl chloride followed by hydrolysis according to the reaction

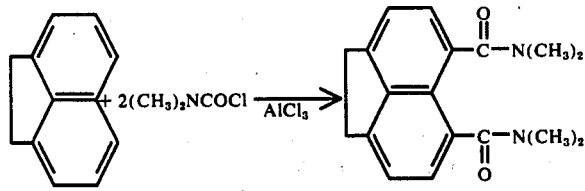

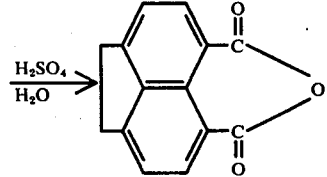

Reaction of (I) with ammonium hydroxide results in

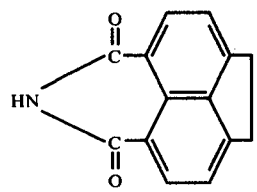

and oxidation of (II) with sodium dichromate yields

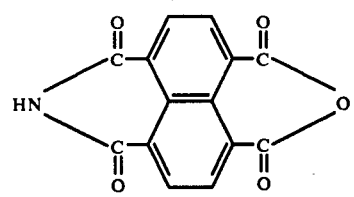

Reaction of (III) with 4-carboxy-o-phenylenediamine in glacial acetic acid and followed by reaction with thionyl chloride yields (V) according to the following:

Thereafter, an amine which may be either a substituted or unsubstituted phenylamine, or a substituted or unsubstituted anthraquinonylamine is reacted with (V) by heating the two components, preferably above 100° C in a solvent such as chlorobenzene, dichlorobenzene, trichlorobenzene, nitrobenzene or 1-chloronaphthalene to give

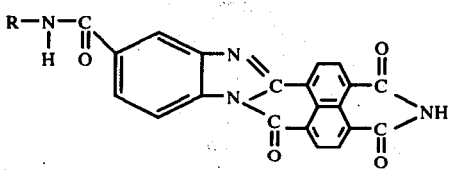

wherein R is previously defined.

Exemplary of amines which may be reacted with (V) are:
aniline;
4-chloroaniline;
2,5-dichloroaniline;
2,4-dichloroaniline;
3,4-dichloroaniline;
2,4,5-trichloroaniline;
4-methylaniline;
4-methoxyaniline;
2,5-dimethoxyaniline;
2-nitro-4-methoxyaniline;
3-chloro-4-methylaniline;
5-chloro-2,4-dimethoxyaniline;
1-aminoanthraquinone;
and the like.

DESCRIPTION OF THE PREFERRED EMBODIMENTS

The following examples are given by way of illustration only.

EXAMPLE I

A mixture of 1 mole of acenaphthene, 2.5 moles of dimethylcarbamoylchloride and 2.6 moles of anhydrous aluminum chloride in chlorobenzene is heated for 3 hours at 130° C. The product is refluxed for 20 minutes in 60 percent $H_2SO_4$ to yield acenaphthene-5,6-dicarboxylic anhydride. This product is refluxed with ammonium hydroxide for several hours, dried and oxidized with sodium dichromate in glacial acetic acid for 3 hours yielding a product identified as 2-hydrobenzo [de]isoquinoline-1,3-dione-6,7-dicarboxylic anhydride.

19 grams of the product obtained and 11 grams of 3,4-diaminobenzoic acid in 350 grams of glacial acetic acid are brought to reflux within 30 minutes with stirring. A thick yellow precipitate forms quickly. Refluxing is continued for 8 hours and the precipitate is filtered, washed with glacial acetic acid and then water to yield 26 grams of (IV) (identified above). The addition of (IV) to 300 grams of nitrobenzene and 15 grams of thionyl chloride and heating at 135° C for 3 hours, subsequent cooling, filtering and washing with benzene yields 27 grams of bright yellow product identified as 9-chloroformylbenzimidazo[2,1-b]-2-hydrobenzo[1mn]-3,8-phenanthroline-1,3,6-trione.

27 grams of this product and 9 grams of 4-chloroaniline in 500 grams of o-dichlorobenzene are brought to reflux within 1 hour with stirring. A thick yellow precipitate forms quickly. Refluxing is continued for 8 hours and the precipitate is filtered, washed with o-dichlorobenzene and then methanol to yield 33 grams of a strongly colored yellow pigment exhibiting excellent fastness to light, temperature stability and resistance to solvents. The product is identified as 9-[1'λ phenyl(4'chloro) carbamoyl]-benzimidazo[2,1-b]-2-hydrobenzo[1mn]-3,8-phenanthroline-1,3,6-trione.

EXAMPLES II – XI 27 grams of 9-chloroformylbenzimidazo[2,1-b]-2-hydrobenzo[1mn]-3,8-phenanthroline-1,3,6-trione are added to 500 grams of o-dichlorobenzene and the temperature is raised to 100° C. While stirring well, 11 grams of 2,3-dichloroaniline are added and the whole is brought to reflux within 30 minutes. A thick yellow precipitate quickly forms. It is refluxed for 8 hours, filtered hot, washed with o-dichlorobenzene then with methanol and dried to yield 35 grams of a strongly colored yellow pigment which is distinguished by excellent fastness to light, temperature stability, and resistance to solvents.

If the 11 grams of 2,3-dichloroaniline are replaced by equimolar amounts of one of the following diamines given below, then with the same procedure, similar fast pigments are obtained.

| Example No. | Amine | Shade |
|---|---|---|
| III | 2,4-dichloroaniline | yellow |
| IV | 2,5-dichloroaniline | yellow |
| V | 3,4-dichloroaniline | yellow |
| VI | 2,4,5-trichloroaniline | yellow |
| VII | 4-methylaniline | orange |
| VIII | 4-methoxyaniline | brown |
| IX | 2,5-dimethoxyaniline | brown |
| X | aniline | orange |
| XI | 1-aminoanthraquinone | yellow |
| XII | 2,4-dimethylaniline | orange |
| XIII | 2,4,6-trimethylaniline | orange |
| XIV | 3,4,5-trimethoxyaniline | brown |
| XV | 3-chloro-4-methylaniline | orange |
| XVI | 3-chloro-6-methoxyaniline | orange |
| XVII | 5-chloro-2,4-dimethoxyaniline | orange |
| XVIII | 3-methyl-6-methoxyaniline | orange |
| XIX | 4-methoxy-2-nitroaniline | yellow |
| XX | 4-chloro-2-nitroaniline | yellow |
| XXI | 4-methyl-2-nitroaniline | yellow |

EXAMPLE XXII 28 grams of 9-chloroformylbenzimidazo[2,1-b]-2-methylbenzo[1mn]-3,8-phenathroline-1,3,6-trione and 9 grams of 4-chloroaniline in 500 grams of o-dichlorobenzene are brought to reflux within 1 hour with stirring. A thick yellow precipitate forms quickly. Refluxing is continued for 8 hours and the precipitate is filtered, washed with o-dichlorobenzene and then methanol to yield 33 grams of a strongly colored yellow pigment exhibiting excellent fastness to light, temperature stability and resistance to solvents. The product is identified as 9-[1'phenyl(4'chloro)carbamoyl]-benzimidazo[2,1-b]-2-methylbenzo[1mn]-3,8-phenanthroline-1,3,6-trione.

I claim:
1. A compound having the formula

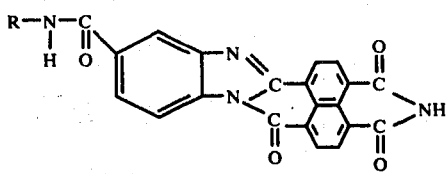

wherein R is phenyl, anthraquinonyl, chlorophenyl, dichlorophenyl, trichlorophenyl, methylphenyl, dimethylphenyl, trimethylphenyl, methoxyphenyl, dimethoxyphenyl, trimethoxyphenyl, (chloro)-(methyl)phenyl, (chloro)(methoxy)phenyl, (chloro)(dimethoxy)phenyl, (methyl)(methoxy)phenyl, (methoxy)(nitro)phenyl, (chloro)(nitro)-phenyl or (methyl)(nitro)-phenyl.

2. A compound as defined in claim 1 wherein R is phenyl.

3. A compound as defined in claim 1 wherein R is chlorophenyl.

4. A compound as defined in claim 1 wherein R is dichlorophenyl.

5. A compound as defined in claim 1 wherein R is trichlorophenyl.

6. A compound as defined in claim 1 wherein R is methylphenyl.

7. A compound as defined in claim 1 wherein R is methoxyphenyl.

8. A compound as defined in claim 1 wherein R is dimethylphenyl.

9. A compound as defined in claim 1 wherein R is trimethylphenyl.

10. A compound as defined in claim 1 wherein R is dimethoxyphenyl.

11. A compound as defined in claim 1 wherein R is trimethoxyphenyl.

12. A compound as defined in claim 1 wherein R is anthraquinonyl.

13. A compound as defined in claim 1 wherein R is (chloro)(methyl)phenyl.

14. A compound as defined in claim 1 wherein R is (chloro)(methoxy)phenyl.

15. A compound as defined in claim 1 wherein R is (chloro)(dimethoxy)phenyl.

16. A compound as defined in claim 1 wherein R is (methyl)(methoxy)phenyl.

17. A compound as defined in claim 1 wherein R is (methoxy)(nitro)phenyl.

18. A compound as defined in claim 1 wherein R is (chloro)(nitro)phenyl.

19. A compound as defined in claim 1 wherein R is (methyl)(nitro)phenyl.

* * * * *